United States Patent [19]
Verrelst et al.

[11] Patent Number: 5,874,661
[45] Date of Patent: Feb. 23, 1999

[54] HYDROCARBON TREATMENT

[75] Inventors: Wim Herman Verrelst, Edegem; Luc Roger Marc Martens, Meise; Georges Marie Karel Mathys, Bierbeek, all of Belgium

[73] Assignee: Exxon Chemical Patents Inc., Houston, Tex.

[21] Appl. No.: 564,114

[22] PCT Filed: Jun. 14, 1994

[86] PCT No.: PCT/EP94/01937

§ 371 Date: May 3, 1996

§ 102(e) Date: May 3, 1996

[87] PCT Pub. No.: WO94/29246

PCT Pub. Date: Dec. 22, 1994

[30] Foreign Application Priority Data

Jun. 14, 1993 [GB] United Kingdom .................. 9312245

[51] Int. Cl.$^6$ ........................................................ C07C 5/27
[52] U.S. Cl. ........................................................... 585/671
[58] Field of Search ............................................. 585/671

[56] References Cited

U.S. PATENT DOCUMENTS

| | | | |
|---|---|---|---|
| 4,885,925 | 12/1989 | Harandi ................................. | 585/331 |
| 5,019,661 | 5/1991 | Mole ..................................... | 585/253 |
| 5,157,194 | 10/1992 | Rahmim et al. ...................... | 585/671 |
| 5,182,247 | 1/1993 | Kuhlmann et al. .................... | 502/217 |
| 5,321,194 | 6/1994 | Apelian et al. ....................... | 585/671 |
| 5,463,161 | 10/1995 | Gajda et al. .......................... | 585/671 |
| 5,516,959 | 5/1996 | Rahmim et al. ...................... | 585/671 |

*Primary Examiner*—Bekir L. Yildirim
*Attorney, Agent, or Firm*—John F. Hunt; Catherine L. Bell

[57] ABSTRACT

The average degree of branching of a branched olefin feedstock is reduced by skeletal isomerization in contact with a molecular sieve.

17 Claims, No Drawings

HYDROCARBON TREATMENT

This application is a 371 filing based on international application PCT/EP94/01937, filed Jun. 14, 1994, which in turn is based on GB application 9312245.5 filed Jun. 14, 1993.

This invention relates to the treatment of hydrocarbons, especially branched aliphatic hydrocarbons, and more especially olefinic hydrocarbons, to effect isomerization of the hydrocarbon skeleton.

Olefinic hydrocarbons are employed as starting materials in the hydroformylation, or oxo, process, for the eventual manufacture of numerous valuable products, e.g., alcohols, esters and ethers derived therefrom, aldehydes, and acids. In many of those end uses, linear or lightly branched hydrocarbon chains have advantages compared with more heavily branched chains.

In the oxo process itself, moreover, olefins with heavily branched chains are less reactive than those with linear or lightly branched structures and, for a given degree of branching, certain isomers are less reactive than others.

Olefinic feedstocks, especially in the $C_4$ to $C_{20}$, and more particularly in the $C_6$ to $C_{15}$ range, are frequently produced by oligomerization of lower molecular weight original starting materials, a process that, because of rearrangements that take place during the reaction, may produce an undesirably high proportion of multiply branched olefins, even if the original materials are linear. Also, the locations of the branches, at sites close to each other on the hydrocarbon chain, or in the central region of the chain, or both, resulting from the oligomerization further reduce the reactivity of the molecules in the oxo reaction.

There are other areas in which a less highly branched hydrocarbon has advantages; these include the alkylation of aromatic hydrocarbons by reaction with olefins in the manufacture of surfactants and polyolefin stabilizers.

There is accordingly a need to provide a method to reduce the degree of branching of a hydrocarbon material.

It has now been found that contacting a branched olefinic hydrocarbon material with a catalyst in the form of a molecular sieve having a 10-membered ring pore structure reduces the degree of branching of the material.

This finding is surprising since more highly branched isomers are thermodynamically more stable than less highly branched isomers. The finding is also surprising in view of the teachings of EP-B-247802 that a linear olefin may be isomerized to a branched olefin by contacting it with a zeolite having such a structure, for example ZSM-23, examples being given of isomerization of n-butene to isobutene.

U.S. Pat. No. 5,157,194 obtains similar results when employing microcrystalline ZSM-22, another 10-numbered ring zeolite, reporting high yields of isobutene from an n-butene feed.

In WO 91/18851, there is disclosed a process for interconversion, including isomerization, of unsaturated compounds, e.g., n-olefins containing 3 to 9 carbon atoms, using a catalyst comprising a molecular sieve ion-exchanged with a cation to provide a Lewis acid site. Suitable molecular sieves include silica/alunina phosphates (SAPO) and zeolites. Favored conditions for isomerization include a temperature in the range 250° to 500° C., especially 375° to 475° C., and a pressure of 0.08 to 0.12 MPa, especially about atmospheric, n-butene readily isomerizing to iso-butene.

EP-A-523838 describes a similar process of isomerizing linear alkenes to branched alkenes, while WO 93/03118 describes a process in which an alkene feed is contacted with two catalysts sequentially for increasing the branched alkene content.

The present invention provides a method of reducing the degree of branching of a branched olefinic feedstock, which comprises contacting it under conditions facilitating skeletal isomerization with a molecular sieve having a 10-membered ring pore structure.

The invention is applicable to all branched olefinic species, but is especially applicable to olefins having from 4 to 20 carbon atoms, more especially to olefins having from 7 to 16 carbon atoms, and particularly alkenes having from 7 to 12 carbon atoms. The feedstock to the reaction may be a single species, a mixture of two or more alkene isomers having the same number of carbon atoms, or a mixture of two or more alkenes having a range of carbon atoms, for example a $C_7$ to $C_{12}$ mixture.

The invention is especially applicable to mixtures of olefinic species having a degree of branching in excess of 1.80, especially in excess of 1.95, more especially mixtures of nonenes having such a degree of branching. The degree of branching (D) of a mixture of olefins having different numbers of branches is defined as follows:

$$D = \frac{my + nz + \text{etc}}{x + y + 2 + \text{etc}}$$

where x is the molar proportion of unbranched species; y is the molar proportion of species having m branches z is the molar proportion of species having n branches, etc.

As examples of molecular sieves having a 10-membered ring pore there may be mentioned the 10-membered ring representatives of tho aluminosilicates, aluminophosphates (AlPO), silicoaluminophosphates (SAPO) metalloaluminophosphates (MeAPO), and metalloalluminophosphosilicates (MeAPSO). More especially, however, there may be mentioned 10-membered ring zeolites, e.g., ZSM-5, ZSM-22, ZSM-23, ZSM-48 and ISI-1 and KZ-2. The zeolites are conveniently used in their acidic ($H^1$) form, either in the dehydrated or the partially hydrated state. The degree of hydration may be controlled by the zeolite calcination conditions when removing the organic template (structure directing agent) if used in the manufacture of the zeolite or by hydration of the feed.

Calcination of the zeolite, if necessary because of the presence of a template, may be effected before use, either in an inert or oxidizing atmosphere, conveniently at temperatures within the range of from 350° to 550° C.

The catalyst may be in powder, granule or other shaped form, e.g., an extrudate produced in admixture with a suitable binder. The catalyst may be readily regenerated, for example by a coke burn in air at a temperature of from 350° to 700° C., advantageously 400° to 5500° C., or by steam treatment, advantageously at 350 ° to 550° C.

A wide range of conditions is available for the isomerization reaction. Isomerization may advantageously be effected at a temperature within the range of from 50° to 350° C., preferably from 150° C. to 250° C. An advantageous pressure for the reaction is within the range of from atmospheric to 10 MPa, preferably from atmospheric to 7.5 MPa. The reaction may be carried out with the feedstock, reaction mixture and product in the gas, liquid, gas/liquid, or dense phase, depending on the temperature and pressure used. The feedstock may consist essentially of the olefin reactant or it may comprise the olefin in admixture with an inert diluent or solvent, for example an alkane, as carrier.

The reaction may be carried out as a batch process, for example in an autoclaver or as a continuous process. In a continuous process, the WHSV of active feedstock is advantageously within the range of from 0.25 to 5 w/wh, preferably from 1 to 2 w/wh.

In addition to reducing the average degree of branching of a mixed olefin feed, the process of the present invention also changes the location of the branch or branches in the olefin feedstock. The effect of this change is generally to increase the number of carbon atoms between branches, resulting in a product in which the branches are further apart and further away from the centre of the molecule. Of course, in an olefin feedstock with a mixture of numbers and locations of branches, it is not possible to identify the reactions individually, but overall the observation is as indicated above.

Using a mixed nonene feed, for example, the result may be summarized in that in addition to reducing the proportion of dimethyl heptenes and increasing that of methyl octenes, the proportion of 3,4-dimethylheptenes decreases while that of 2,5-dimethylheptenes is increased.

The isomerization reaction may be used alone or in combination with other reactions, either simultaneously or sequentially.

The present invention accordingly also provides a process in which an olefin or a non-olefinic starting material is converted into a branched olefin, the resulting olefin is contacted under conditions facilitating isomerization with a molecular sieve having a 10-membered ring pore structure, and, if desired or required, the isomerized olefin product is converted into a different olefinic or non-olefinic species.

The invention also provides a process in which a branched olefin is contacted under conditions facilitating isomerization with a molecular sieve having a 10-membered ring pore structure, and the isomerized olefin product is converted into a different olefinic or a non-olefinic species, the branched olefin having been formed, if desired or required, from a non-olefinic or an olefinic species different from that isomerized.

As an example of a process in which the starting material or final product is non-olefinic, there may be mentioned the process mentioned above in which the isomerized olefin product is subjected to hydroformylation.

As an example of a reaction sequence in which the starting material is a different olefinic species from that isomerized, there may be mentioned that in which a low molecular weight olefin, for example, propene or butene, is oligomerized to a higher molecular weight olefin, e.g., octene, nonene or dodecene, and the higher molecular weight olefin isomerized as described above, the isomerized olefin then optionally being used as a hydroformylation feed or further oligomerized.

Such a sequence may be carried out by oligomerization of a light olefin feed employing, for example, solid phosphoric acid, H-ZSM-5, acidic silica, alumina or mixed silica/alumina, or a transition metal-based oligomerization catalyst, as catalyst to give an oligomer mixture which has a high degree of branching, then skeletally isomerizing the mixture by the process of the invention, if desired fractionating the oligomer mixture beforehand. The product may be further oligomerized or used as feed to hydroformylation.

The oligomerization and the subsequent isomerization may be carried out in different reactors, which is preferred isomerization is not always required. This may be the case where the initial oligomerization sometimes does and sometimes does not give rise to an oligomer mixture or a downstream product according to an existing specification; the oligomer may be analyzed and the isomerization reactor brought on stream when necessary.

When, in contrast, isomerization is always required then, since the reaction conditions for oligomerization and isomerization are substantially the same, the oligomerization and isomerization catalyst may be placed in the same reactor either in series or in admixture. Mixtures of catalysts in the same bed are advantageously mixtures of two zeolite catalysts, e.g., ZSM-5 and ZSM-22.

As well as or, preferably, instead of isomerizing the oligomer olefin feed to a reactor, e.g., a hydroformylation reactor, isomerization may be carried out on unreacted olefin separated from the reaction product leaving the reactor, and recycled to the reactor. As indicated above, heavily branched olefins are less reactive in the oxo process than are less lightly branched isomers.

Since not all the olefin in the feedstock is converted to oxygenated product in normal commercial operation of the oxo process, unreacted starting materials are separated from the oxygenated product and recycled. This eventually results in a serious loss of efficiency as the less reactive species build up in the recycled material as the reaction proceeds.

By employing the skeletal isomerization process of the present invention on the unreacted olefins, these may be converted into more reactive species before recycling. The invention accordingly more especially provides a process for hydroformylating an olefin feedstock in which after hydroformylation, unreacted olefin is separated from reaction product, contacted under isomerization conditions with a molecular sieve having a 10-membered ring pore structure, and returned to the hydroformylation reaction.

This process has the advantage that it enables the hydroformylation to be carried out at a lower conversion rate, thereby reducing by-products, e.g., heavy species and paraffins, and facilitates lower oxo catalyst consumption. Additionally, the average reactivity of the olefin feed to the reactor is increased more efficiently if only unreacted olefin is subjected to the isomerization reaction since this will have a higher degree of branching than the initial feed.

The following Examples illustrate the invention:

EXAMPLE 1

In this example, a dilute branched nonene feed is used as feedstock in a continuous process. The conditions, resulting in a dense phase feed, were as follows:

| Feed | 3% by weight nonene fraction in propane |
| --- | --- |
| Catalyst | H-ZSM-22 |
| Space Velocity | 1.6 g/gh. (based on nonene content) |
| Temperature | 200° C. |
| Pressure | 7 MPa |
| Reactor | Continuous flow, fixed bed |
| Duration | 5 hours |
| Reactive feed Composition by weight | $C_8^-$ 0.8% $C_9^+C_{10}$ 97.6% $C_{11}^+$ 1.6% |

Table 1 below shows the composition, in terms of branching of the nonene fraction, of the feed and of the product as collected over various time periods. All such analyses are carried out by gas chromatography after on-line hydrogenation.

TABLE 1

| | ISOMERS % | | | | |
| --- | --- | --- | --- | --- | --- |
| Isomers | LINEAR | 1-Br | 2-Br | 3-Br | D |
| FEED PRODUCT: | 1.22 | 8.81 | 75.96 | 14.01 | 2.03 |
| 0.6 to 1.1 h | 0.00 | 26.54 | 62.60 | 10.86 | 1.84 |
| 2.2 to 2.6 h | 1.30 | 26.57 | 59.35 | 12.79 | 1.84 |
| 4.3 to 4.7 h | 0.68 | 27.23 | 60.88 | 11.21 | 1.83 |

Abbreviations:
h - hour
1-Br, etc = singly branched, etc.
D = Degree of Branching.

Table 2 below shows the mole fraction of the various isomers of nonene in the feed and the product over various time periods.

TABLE 2

| Isomers | FEED | 0.6 to 1.1 h | 2.2 to 2.6 h | 4.3 to 4.7 h |
|---|---|---|---|---|
| 2,2,5 Tri Me Hexane | 1.19 | 2.82 | 3.18 | 2.97 |
| 2,2,4 Tri Me Hexane | 0.75 | 0.48 | 0.52 | 0.82 |
| 2,3,5 Tri Me Hexane | 3.71 | 4.50 | 4.20 | 4.34 |
| 2,2 Di Me Heptane | 1.74 | 1.46 | 1.66 | 1.72 |
| 2,4 Di Me Heptane | 10.04 | 9.46 | 8.99 | 9.44 |
| 2 Me 4 Et Hexane | 3.48 | 2.87 | 3.14 | 3.04 |
| 2,6 Di Me Heptane | 3.89 | 5.50 | 5.65 | 5.47 |
| 2,5 Di Me Heptane | 21.23 | 22.56 | 22.87 | 22.73 |
| 3,5 Di Me Heptane | 0.00 | 1.44 | 0.00 | 1.02 |
| 2,4 Di Me 3 Et Pentane | 2.85 | 1.13 | 1.64 | 0.99 |
| 2,3,3 Tri Me Hexane | 1.07 | 0.28 | 0.88 | 0.36 |
| 2 Me 3 Et Hexane | 4.32 | 2.05 | 2.10 | 1.91 |
| 2,3,4 Tri Me Hexane | 2.43 | 0.96 | 1.14 | 0.98 |
| 3,3,4 Tri Me Hexane | 2.02 | 0.69 | 1.22 | 0.76 |
| 2,3 Di Me Heptane | 13.50 | 7.80 | 6.65 | 7.28 |
| 3,4 Di Me Heptane | 17.77 | 9.45 | 8.28 | 8.26 |
| 4 Me Octane | 2.70 | 8.30 | 8.15 | 9.09 |
| 2 Me Octane | 1.66 | 6.45 | 6.28 | 5.97 |
| 3 Et Heptane | 1.01 | 2.01 | 2.44 | 1.95 |
| 3 Me Octane | 3.45 | 9.78 | 9.70 | 10.21 |
| n Nonane | 1.22 | 0.00 | 1.30 | 0.68 |

Table 3 shows the proportions, in weight percent, of species of various carbon number ranges in the feed and the product over various time periods, as determined by gas chromatography.

TABLE 3

|  | Feed | 0.6 to 1.1 h | 1.7 to 2.2 h | 4.3 to 4.7 h |
|---|---|---|---|---|
| up to $C_8$ | 0.8 | 2.3 | 1.5 | 1.2 |
| $C_9$ and $C_{10}$ | 97.6 | 84.0 | 89.9 | 93.8 |
| greater than $C_{10}$ | 1.6 | — | — | — |
| $C_{11}$ to $C_{16}$ | — | 6.2 | 4.5 | 1.7 |
| $C_{18}$ | — | 7.5 | 5.3 | 3.3 |

The results in Tables 1 to 3 above indicate a decrease in the degree of branching of the nonenes, primarily from a decrease in di-branching and an increase in single branching, accompanied by a decrease in 2,3- and 3,4-dimethyl heptenes and an increase in 2,5- and 2,6-isomers. No significant deactivation of the catalyst was observed over the duration or the test.

EXAMPLE 2

In this example, an undiluted nonene was used in a batch process. The reaction conditions were as follows:

| Feed | 100% nonene fraction, composition as in Example 1. |
|---|---|
| Catalyst | H-ZSM 22, 10% by weight of feed. |
| Temperature | 200° C. |
| Pressure | 300 kPa |
| Phase | Liquid |
| Reactor | Stirred autoclave |
| Duration | 9.5 hours. |

Table 4 shows the composition, in terms of branching of the nonene fraction, of the feed and the reaction mixture as sampled at the times shown.

TABLE 4

|  | ISOMERS, % | | | | |
|---|---|---|---|---|---|
|  | LINEAR | 1-Br | 2-Br | 3-Br | D |
| FEED Product | 0.9 | 6.0 | 86.3 | 6.6 | 1.98 |
| 1.5 h | 0.8 | 10.5 | 81.9 | 6.8 | 1.95 |
| 3.5 h | 2.0 | 19.2 | 71.8 | 7.0 | 1.84 |
| 9.5 h | 1.4 | 26.9 | 63.9 | 7.8 | 1.78 |

Table 5 shows the mole fraction of isomers of di-branched nonenes after various times.

TABLE 5

|  | FEED | 1.5 h | 3.5 h | 9.5 h |
|---|---|---|---|---|
| 26 | 3.7 | 7.9 | 10.0 | 13.3 |
| 25 + 35 | 30.8 | 31.7 | 35.6 | 40.1 |
| 24 | 13.5 | 13.1 | 13.3 | 13.7 |
| 23 + 3E3M | 16.8 | 15.6 | 14.1 | 11.8 |
| 22 | 1.6 | 2.0 | 2.1 | 2.2 |
| 2M3E + 234)* | 10.5 | 9.5 | 8.3 | 5.7 |
| 34 + 4E | 22.7 | 19.9 | 16.9 | 13.3 |

*No separation of GC peaks obtained.
Abbreviations:
26,etc = 2,6-dimethylheptenes, etc
3E3M, etc = 3-ethyl-3-methylhexenes, etc
234 = 2,3,4-trimethylhexenes.

The results in Tables 4 and 5 show that after 9.5 hours the product distribution, as indicated by the nonene isomers, is very similar to that of Example 1, as shown in Tables 1 and 2.

EXAMPLE 3

The reaction was carried out in an autoclave under autogenous pressure, with the temperature being maintained at 165° C., for 24 hours. The feed was 50 g of an isomeric mixture of heptenes, the catalyst was 10 g of H-ZSM-22 powder.

Table 6 shows the composition of the feed and the final product.

TABLE 6

|  | FEED | PRODUCT |
|---|---|---|
| Heptene Isomers | | |
| 2,2 Di Me Pentane | 2.28 | 0.53 |
| 2,4 Di Me Pentane | 18.20 | 14.63 |
| 2,2,3 Tri Me Pentane | 0.59 | 2.03 |
| 3,3 Di Me Pentane | 0.33 | 0.00 |
| 2 Me Hexane | 15.05 | 29.55 |
| 2,3 Di Me Pentane | 36.06 | 29.47 |
| 3 Me Hexane | 21.79 | 18.86 |
| 3 Et Pentane | 2.62 | 1.41 |
| n Heptane | 3.08 | 3.52 |
| Heptene isomer distribution | | |
| Linear | 3.08 | 3.52 |
| Mono-branched | 39.47 | 49.82 |
| Di-branched | 56.86 | 44.63 |
| Tri-branched | 0.59 | 2.03 |
| D | 1.55 | 1.45 |

EXAMPLE 4

In this example, carried out like Example 3 in an autoclave at autogenous pressure, the feed was a mixture of octene and nonene isomers with the octenes forming the major fraction. 10% by weight, based on the weight of feed, of H-ZSM-22-catalyst was employed, and the temperature maintained at 190° C., for 24 hours. The results are shown in Tables 7 and 8.

TABLE 7

|  | FEED | PRODUCT |
|---|---|---|
| Octene Isomers |  |  |
| 2,2,4 Tri Me Pentane | 0.14 | 0.00 |
| 2,2 Di Me Hexane | 3.77 | 5.33 |
| 2,5 Di Me Hexane | 12.84 | 12.98 |
| 2,4 Di Me Hexane | 18.07 | 18.61 |
| 2,2,3 Tri Me Pentane | 3.21 | 3.45 |
| 3,3 Di Me Hexane | 3.43 | 2.30 |
| 2,3,4 Tri Me Pentane | 8.36 | 8.99 |
| 2,3,3 Tri Me Pentane | 1.37 | 1.34 |
| 2,3 Di Me Hexane | 18.93 | 14.76 |
| 2 Me 3 Et Pentane | 0.00 | 0.00 |
| 2 Me Heptane | 5.04 | 6.89 |
| 4 Me Heptane | 3.95 | 3.64 |
| 3,4 Di Me Hexane | 10.85 | 9.99 |
| 3 Me Heptane | 7.20 | 10.27 |
| n Octane | 2.85 | 1.45 |
| Octene Isomer Distribution |  |  |
| Linear | 2.85 | 1.45 |
| Mono-branched | 16.18 | 20.80 |
| Di-branched | 67.88 | 63.97 |
| Tri-branched | 13.09 | 13.78 |
| D | 1.91 | 1.90 |

TABLE 8

|  | FEED | PRODUCT |
|---|---|---|
| Nonene Isomers |  |  |
| 2,2,5 Tri Me Hexane | 13.54 | 14.95 |
| 2,2,4 Tri Me Hexane | 9.08 | 3.49 |
| 2,3,5 Tri Me Hexane | 10.85 | 14.47 |
| 2,2 Di Me Heptane | 8.67 | 2.38 |
| 2,4 Di Me Heptane | 12.83 | 9.22 |
| 2 Me 4 Et Hexane | 4.67 | 4.61 |
| 2,6 Di Me Heptane | 5.02 | 2.59 |
| 2,5 Di Me Heptane | 10.80 | 11.60 |
| 3,5 Di Me Heptane | 0.00 | 4.05 |
| 2,4 Di Me 3 Et Pentane | 4.31 | 1.68 |
| 2,3,3 Tri Me Hexane | 2.08 | 0.28 |
| 2 Me 3 Et Hexane | 3.04 | 2.45 |
| 2,3,4 Tri Me Hexane | 1.93 | 1.82 |
| 3,3,4 Tri Me Hexane | 1.22 | 1.33 |
| 2,3 Di Me Heptane | 4.61 | 9.22 |
| 3,4 Di Me Heptane | 4.06 | 7.90 |
| 4 Me Octane | 1.52 | 2.38 |
| 2 Me Octane | 0.00 | 2.03 |
| 3 Et Heptane | 0.00 | 0.28 |
| 3 Me Octane | 1.22 | 3.28 |
| n Nonane | 0.00 | 0.00 |
| Nonene isomer distribution |  |  |
| Linear | 0.00 | 0.00 |
| Mono-branched | 2.74 | 7.97 |
| Di-branched | 53.70 | 54.02 |
| Tri-branched | 43.56 | 38.02 |
| D | 2.41 | 2.30 |

EXAMPLE 5

Example 4 was repeated, but using 20% by weight of catalyst. The results are shown in Tables 9 and 10 below.

TABLE 9

|  | FEED | PRODUCT |
|---|---|---|
| Octene Isomers |  |  |
| 2,2,4 Tri Me Pentane | 0.14 | 0.00 |
| 2,2 Di Me Hexane | 3.77 | 1.90 |
| 2,5 Di Me Hexane | 12.84 | 12.14 |
| 2,4 Di Me Hexane | 18.07 | 18.38 |
| 2,2,3 Tri Me Pentane | 3.21 | 1.54 |
| 3,3 Di Me Hexane | 3.43 | 1.07 |
| 2,3,4 Tri Me Pentane | 8.36 | 4.36 |
| 2,3,3 Tri Me Pentane | 1.37 | 0.75 |
| 2,3 Di Me Hexane | 18.93 | 11.48 |
| 2 Me 3 Et Pentane | 0.00 | 0.00 |
| 2 Me Heptane | 5.04 | 12.89 |
| 4 Me Heptane | 3.95 | 5.90 |
| 3,4 Di Me Heptane | 10.85 | 6.28 |
| 3 Me Heptane | 7.20 | 18.98 |
| n Octane | 2.85 | 4.33 |
| Octene Isomer Distribution |  |  |
| Linear | 2.85 | 4.33 |
| Mono-branched | 16.18 | 37.77 |
| Di-branched | 67.88 | 51.25 |
| Tri-branched | 13.09 | 6.65 |
| D | 1.91 | 1.60 |

TABLE 10

|  | FEED | PRODUCT |
|---|---|---|
| Nonene Isomers |  |  |
| 2,2,5 Tri Me Hexane | 13.54 | 12.91 |
| 2,2,4 Tri Me Hexane | 9.08 | 4.91 |
| 2,3,5 Tri Me Hexane | 10.85 | 12.30 |
| 2,2 Di Me Heptane | 8.67 | 1.67 |
| 2,4 Di Me Heptane | 12.83 | 7.44 |
| 2 Me 4 Et Hexane | 4.67 | 2.94 |
| 2,6 Di Me Heptane | 5.02 | 4.71 |
| 2,5 Di Me Heptane | 10.80 | 16.61 |
| 3,5 Di Me Heptane | 0.00 | 0.00 |
| 2,4 Di Me 3 Et Pentane | 4.31 | 1.87 |
| 2,3,3 Tri Me Hexane | 2.08 | 0.00 |
| 2 Me 3 Et Hexane | 3.04 | 1.16 |
| 2,3,4 Tri Me Hexane | 1.93 | 2.03 |
| 3,3,4 Tri Me Hexane | 1.77 | 1.57 |
| 2,3 Di Me Heptane | 4.61 | 5.06 |
| 3,4 Di Me Heptane | 4.06 | 5.52 |
| 4 Me Octane | 1.52 | 5.42 |
| 2 Me Octane | 0.00 | 5.06 |
| 3 Et Heptane | 0.00 | 1.47 |
| 3 Me Octane | 1.22 | 7.34 |
| n Nonane | 0.00 | 0.00 |
| Nonene isomer distribution |  |  |
| Linear | 0.00 | 0.00 |
| Mono-branched | 2.74 | 19.29 |
| Di-branched | 53.70 | 45.11 |
| Tri-branched | 43.56 | 35.59 |
| D | 2.41 | 2.16 |

EXAMPLE 6

Example 4 was repeated, but using as feed an octene mixture obtained by the dimerization of isobutylene; the temperature was maintained at 200° C. The results are shown in Tables 11 and 12 below.

TABLE 11

|  | FEED | PPODUCT |
|---|---|---|
| Linear | 0.0 | 0.82 |
| Mono-branched | 0.0 | 17.58 |
| Di-branched | 0.48 | 25.04 |
| Tri-branched | 99.52 | 56.55 |
| D | 3.00 | 2.37 |

TABLE 12

| Octene Isomers | FEED | PRODUCT |
|---|---|---|
| 2,2,4 Tri Me Pentane | 96.14 | 9.70 |
| 2,2 Di Me Hexane | 0.48 | 0.99 |
| 2,5 Di Me Hexane | 0.00 | 5.05 |
| 2,4 Di Me Hexane | 0.00 | 8.43 |
| 2,2,3 Tri Me Pentane | 1.71 | 9.33 |
| 3,3 Di Me Hexane | 0.00 | 1.49 |
| 2,3,4 Tri Me Pentane | 1.16 | 33.13 |
| 2,3,3 Tri Me Pentane | 0.51 | 4.40 |
| 2,3 Di Me Hexane | 0.00 | 5.99 |
| 2 Me 3 Et Pentane | 0.00 | 0.00 |
| 2 Me Heptane | 0.00 | 5.70 |
| 4 Me Heptane | 0.00 | 2.98 |
| 3,4 Di Me Hexane | 0.00 | 3.08 |
| 3 Me Heptane | 0.00 | 8.90 |
| n Octane | 0.00 | 0.82 |

EXAMPLE 7

Example 4 was repeated, but using a nonene feed. The results are shown in Table 13.

TABLE 13

|  | FEED | PRODUCT |
|---|---|---|
| Nonene isomers |  |  |
| 2,2,5 Tri Me Hexane | 1.19 | 3.26 |
| 2,2,4 Tri Me Hexane | 0.75 | 1.26 |
| 2,3,5 Tri Me Hexane | 3.71 | 4.80 |
| 2,2 Di Me Heptane | 1.74 | 1.82 |
| 2,4 Di Me Heptane | 10.04 | 8.41 |
| 2 Me 4 Et Hexane | 3.48 | 3.59 |
| 2,6 Di Me Heptane | 3.89 | 5.46 |
| 2,5 Di Me Heptane | 21.23 | 21.65 |
| 3,5 Di Me Heptane | 0.00 | 0.00 |
| 2,4 Di Me 3 Et Pentane | 2.85 | 1.38 |
| 2,3,3 Tri Me Hexane | 1.07 | 0.86 |
| 2 Me 3 Et Hexane | 4.32 | 2.12 |
| 2,3,4 Tri Me Hexane | 2.43 | 1.72 |
| 3,3,4 Tri Me Hexane | 2.02 | 1.42 |
| 2,3 Di Me Heptane | 13.50 | 7.69 |
| 3,4 Di Me Heptane | 17.77 | 8.25 |
| 4 Me Octane | 2.70 | 8.12 |
| 2 Me Octane | 1.66 | 6.23 |
| 3 Et Heptane | 1.01 | 2.12 |
| 3 Me Octane | 3.45 | 9.85 |
| n Nonane | 1.22 | 0.00 |
| Nonene isomer distribution |  |  |
| Linear | 1.22 | 0.00 |
| Mono-branched | 8.81 | 26.32 |
| Di-branched | 75.96 | 58.98 |
| Tri-branched | 14.01 | 14.70 |
| D | 2.03 | 1.88 |

EXAMPLE 8

In this example, the catalyst was H-ZSM-22 in 3 mm extrudate form used at 10 % by weight of a nonene feed. The isomerization reaction was carried out for 24 hours at 200° C. in an autoclave under autogenous pressure. The results are shown in Table 14.

TABLE 14

|  | FEED | PRODUCT |
|---|---|---|
| Nonene isomer distribution |  |  |
| Linear | 1.22 | 1.49 |
| Mono-branched | 8.81 | 20.50 |
| Di-branched | 75.96 | 65.23 |
| Tri-branched | 14.01 | 12.78 |
| D | 2.03 | 1.89 |
| Nonene isomers |  |  |
| 2,2,5 Tri Me Hexane | 1.19 | 2.46 |
| 2,2,4 Tri Me Hexane | 0.75 | 1.01 |
| 2,3,5 Tri Me Hexane | 3.71 | 4.05 |
| 2,2 Di Me Heptane | 1.74 | 1.48 |
| 2,4 Di Me Heptane | 10.04 | 8.48 |
| 2 Me 4 Et Hexane | 3.48 | 3.90 |
| 2,6 Di Me Heptane | 3.89 | 4.45 |
| 2,5 Di Me Heptane | 21.23 | 17.77 |
| 3,5 Di Me Heptane | 0.00 | 4.77 |
| 2,4 Di Me 3 Et Pentane | 2.85 | 1.77 |
| 2,3,3 Tri Me Hexane | 1.07 | 0.34 |
| 2 Me 3 Et Hexane | 4.32 | 2.67 |
| 2,3,4 Tri Me Hexane | 2.43 | 1.82 |
| 3,3,4 Tri Me Hexane | 2.02 | 1.33 |
| 2,3 Di Me Heptane | 13.50 | 10.19 |
| 3,4 Di Me Heptane | 17.77 | 11.51 |
| 4 Me Octane | 2.70 | 5.62 |
| 2 Me Octane | 1.66 | 5.69 |
| 3 Et Heptane | 1.01 | 1.37 |
| 3 Me Octane | 3.45 | 7.83 |
| n Nonane | 1.22 | 1.49 |

EXAMPLE 9

Example 8 was repeated, but isomerization was carried out for 6 hours only. The results are shown in Table 15.

TABLE 15

|  | FEED | PRODUCT |
|---|---|---|
| Nonene isomers |  |  |
| 2,2,5 Tri Me Hexane | 1.19 | 1.79 |
| 2,2,4 Tri Me Hexane | 0.75 | 0.84 |
| 2,3,5 Tri Me Hexane | 3.71 | 4.00 |
| 2,2 Di Me Heptane | 1.74 | 1.72 |
| 2,4 Di Me Heptane | 10.04 | 8.53 |
| 2 Me 4 Et Hexane | 3.48 | 3.62 |
| 2,6 Di Me Heptane | 3.89 | 3.61 |
| 2,5 Di Me Heptane | 21.23 | 17.13 |
| 3,5 Di Me Heptane | 0.00 | 4.23 |
| 2,4 Di Me 3 Et Pentane | 2.85 | 2.39 |
| 2,3,3 Tri Me Hexane | 1.07 | 0.28 |
| 2 Me 3 Et Hexane | 4.32 | 3.51 |
| 2,3,4 Tri Me Hexane | 2.43 | 2.04 |
| 3,3,4 Tri Me Hexane | 2.02 | 1.47 |
| 2,3 Di Me Heptane | 13.50 | 11.97 |
| 3,4 Di Me Heptane | 17.77 | 14.54 |
| 4 Me Octane | 2.70 | 4.81 |
| 2 Me Octane | 1.66 | 4.25 |
| 3 Et Heptane | 1.01 | 0.95 |
| 3 Me Octane | 3.45 | 7.01 |
| n Nonane | 1.22 | 1.30 |
| Nonene isomer distribution |  |  |
| Linear | 1.22 | 1.30 |
| Mono-branched | 8.81 | 17.02 |
| Di-branched | 75.96 | 68.86 |
| Tri-branched | 14.01 | 12.82 |
| D | 2.03 | 1.93 |

A comparison of Examples 8 and 9 shows that prolonging the isomerization reaction produces a lower degree of branching. This is, however, at the expense of decreasing yield, because of the competing oligomerization reaction.

We claim:

1. A method of isomerizing a branched olefinic feedstock containing at least one olefin having a carbon number within the range of from 4 to 20, which comprises contacting the feedstock under conditions favoring skeletal isomerization with a zeolite free of added catalytic metal selected from the group consisting of ZSM-22, ZSM-23 and ZSM-48 at a temperature in the range of 50° to 350° C., the product of said isomerization having a reduced average degree of branching as compared with said olefin feedstock.

2. The method of claim 1, wherein the feedstock contains at least one olefin having a carbon number within the range of from 7 to 16.

3. The method of claim 1, wherein the feedstock contains at least one alkene with from 7 to 12 carbon atoms.

4. The method of claim 1, wherein the feedstock is a mixture of isomers having the same number of carbon atoms.

5. The method of claim 1, wherein the feedstock is a mixture of olefins having a range of carbon atom numbers.

6. The method of claim 1, wherein the feedstock comprises nonenes.

7. The method of claim 6 wherein the feedstock has a degree of branching in excess of 1.95.

8. The method of claim 1, wherein the zeolite is ZSM-22.

9. The method of claim 1, wherein the zeolite is in the acidic form.

10. The method of claim 1, wherein the zeolite has been calcined.

11. The method of claim 1, wherein the zeolite is in powder, granule or extrudate form.

12. The method of claim 1, carried out at a pressure between atmospheric pressure and 10 MPa.

13. The method of claim 1, wherein the feedstock consists essentially of the branched olefin.

14. The method of claim 1, wherein the feedstock comprises the branched olefin in admixture with a diluent or solvent.

15. The method of claim 1 wherein said temperature is in the range of 150° to 250° C.

16. A method of isomerizing a branched olefinic feedstock containing at least one olefin having a carbon number within the range of from 4 to 20, which comprises contacting the feedstock under conditions favoring skeletal isomerization with a acidic zeolite free of added catalytic metal having a ten membered ring pore structure at a temperature in the range of 50° to 350° C., the product of said isomerization having a reduced average degree of branching as compared with said olefin feedstock.

17. The process of claim 16 wherein said zeolite is ZSM-22.

* * * * *